United States Patent [19]

Vairel et al.

[11] Patent Number: 4,687,765
[45] Date of Patent: Aug. 18, 1987

[54] METHOD AND COMPOSITION FOR THROMBOLYTIC TREATMENT

[75] Inventors: Edmond G. Vairel; Huguette Brouty-Boye; Francis Toulemonde, all of Paris; Christian Doutremepuich, Bordeaux, all of France

[73] Assignee: Choay S.A., Paris, France

[21] Appl. No.: 760,483

[22] Filed: Jul. 30, 1985

Related U.S. Application Data

[63] Continuation of Ser. No. 516,796, Jul. 25, 1983, abandoned.

[51] Int. Cl.⁴ ............................................ A61K 31/725
[52] U.S. Cl. ...................................... 514/56; 514/822
[58] Field of Search .................................. 514/56, 822

[56] References Cited

U.S. PATENT DOCUMENTS 3,118,817 1/1964 Nomine et al. ...................... 514/56
4,500,519 2/1985 Lormeau et al. ..................... 514/56

FOREIGN PATENT DOCUMENTS 8101004 4/1981 European Pat. Off. .............. 514/56
0596240 3/1978 U.S.S.R. ................................ 514/56

Primary Examiner—Johnnie R. Brown
Assistant Examiner—John W. Rollins
Attorney, Agent, or Firm—Weiser & Stapler

[57] ABSTRACT

The invention relates to a method and composition for thrombolytic treatment. It comprises administering to thrombosis-afflicted patients a low molecular weight heparin in an amount effective to cause lysis of thrombi in vivo.

16 Claims, No Drawings

METHOD AND COMPOSITION FOR THROMBOLYTIC TREATMENT

This is a continuation of application Ser. No. 516,796, filed July 25, 1983 now abandoned.

The invention relates to a composition and method for thrombolytic treatment in vivo, particularly in man, which brings into play a heparin fraction of low molecular weight, which will also hereafter be referred to sometimes as LMW heparin, in contrast with standard heparin which will simply be referred to as "heparin".

Heparin is a drug the anticoagulant activities of which are well known. It is widely used in therapy for the control of hypercoagulability risks with the aim of preventing the formation of thrombi in vivo. Treatments based on heparin must be adjusted carefully inasmuch as the administration of an excess of heparin can induce hemorrhages. Therefore under certain circumstances, for instance in post-surgical periods one has been tempted to refrain from administering heparin for fear of such hemorrhages, although the patients concerned were subject to high thromboembolic risks.

It has also been already shown that heparin induces an increase of the level of circulating plasminogen and of the synthesis or excretion thereof by cell cultures as well as by isolated organs. But for fear of the same risks, the use of heparin as the active principle of drugs for causing the lysis in vivo of pre-existing or pre-formed clots have never been considered seriously.

It is now also well known that LMW heparin which can be obtained from heparin either by physical fractionation procedures or by partial depolymerization of heparin, can have strong antithrombotic activities, yet are substantially freed from the hemorrhage-inducing effects. Such LMW heparins are disclosed in U.S. applications Ser. No. 91,164 of J. C. LORMEAU et al, field on Nov. 5, 1979, and in application Ser. No. 323,567 of J. C. LORMEAU et al filed on Nov. 20, and U.S. application Ser. No. 448,639 filed in December 1982, all of which are incorporated herein by reference.

The behaviour of both heparin and of LMW heparin in assays with a view of determining their respective influences on the mechanism of fibrinolysis has also been investigated in vitro. H. VINAZZER et al, in an article titled "Influence of Heparin; of different heparin fractions and of a low molecular weight heparin-like substance on the mechanism of fibrinolysis" (Thrombosis Research 27; 341-352, 1982) have reported that heparin had fibrinolysis-activating properties as a result of assays carried out in vitro and based on the significant shortening of the euglobulin lysis time in the test system disclosed by these authors in the presence of standard polymucosa heparin or hepaxin. A synthetic polysulfated polysaccharide SP 54 having a molecular weight of about 3000 was also found to possess fibrinolysis-activating properties. However LMW heparin having an average molecular weight of 3300 daltons and orginating from heparin was found to be considerably less active than heparin in the same in vitro test. It was thus deemed by these authors that the magnitude of the activation of fibrinolysis partly depends on the molecular weight of the substance but apparently also on the degree of sulfatation since the low molecular weight substance with a high number of sulfate bonds such as the tested SP 54 was also considerably more active than the low molecular weight fraction of standard heparin.

It was thus all the more surprising that LMW heparins could to the contrary have very significant thrombolytic, particularly fibrinolytic properties in vivo. "Thrombolytic" here means the dissolving action which is exerted on a pre-existing thrombus in vivo "Fibrinolytic" refers to the property of lysing insoluble fibrin in vivo. This discovery also underlies the invention which relates to a thrombolytic method in vivo. More particularly the invention pertains to a method for the lysis of blood thrombus, particularly a means comprising administering LMW heparin in an amount effective to lyse the blood thrombus. Particularly the invention relates to a method for the lysis of blood thrombus in vivo comprising administering the LMW heparin in an amount effective to cause lysis of insoluble fibrin in vivo.

More particularly it has been found that LMW heparin can be used with a reasonable degree of safety at the dosages required for inducing the thrombolytic effect in vivo, such dosages being substantially higher than the dosages required for the preventive known anti-thrombotic action. This is in sharp contrast with heparin which at the dosage at which it could, in theory, be active for stimulating thrombolysis or fibrinolysis of the blood clots would then also entail high risks of hemorrhages in vivo.

To the contrary, it has been found that, when using LMW heparin, these risks can be adequately controlled, even at high dosages, even though at said dosages the anti coagulating total activity as measurable by the USP units may be far from negligible.

As concerns the definition of USP units or USP titers, reference is made to the U.S. applications already made of record hereabove.

LMW heparin as herein defined means heparin fractions consisting essentially of constituents having molecular weights less than about 10,000, preferably ranging from about 2000 to 8000. Molecular weights are determined as referred to in the abovesaid applications.

Preferred LMW heparins are those whose Yin-Wessler titers (as defined in the above U.S. application) and USP titers are respectively in a ratio of at least 3. Preferred LMW heparins have USP titers not more than 60 IU/mg particularly not more than 40 I.U/mg. Further preferred LMW heparins meeting these conditions relative to USP titers have YW titers and USP titers which are respectively in ratio ranging from about 4 to about 30.

LMW heparins can be obtained from heparin by any appropriate process, for instance also by any of the processes disclosed in U.S. application Ser. No. 448,639 filed on Dec. 12, 1982, in U.S. Pat. No. 1,303,651 issued on Dec. 1, 1981, in International Application No. SE 8100252/WO82 010005 published on Apr. 1, 1982, in European patent application Nos. 81301825.6/0041771 published on Dec. 16, 1981, 81 400728/0040144 published on Nov. 18, 1981, in French patent application Nos. 78 23499/2 400037 published on Mar. 9, 1979 and 81 01508/2 474508 published on July 31, 1981, etc. All these patent or patent applications or their American counterpart patent applications or patents where appropriate are incorporated herein by reference.

It must be understood that the invention deals with pharmaceutical compositions and methods of thrombolytic treatment at a curative level, that is for remedying to the pathological effects resulting more particularly from arterial or venous thrombosis. Accordingly the LMW heparin can be substituted for streptokinase or urokinase in the thrombolytic or fibrinolytic treatments in which these drugs have been found to be useful.

The invention also relates to pharmaceutical preparations which include said LMW heparins in amounts effective to cause thrombolysis or fibrinolysis in vivo in association with pharmaceutical excipients.

In particular, it relates to compositions in which the pharmaceutical vehicle is suitable for oral administration. Suitable administration forms of the invention for oral use can advantageously be gastro-resistant capsules, tablets or pills.

Other pharmaceutical compositions comprise these LMW heparins in association with suitable excipients for rectal administration. Corresponding administration forms are constituted by suppositories.

Preferably however the pharmaceutical preparations consist of sterile or sterilizable injectable compositions, particularly are intended for continuous perfusion or for parenteral administration, particularly intravenous, intramuscular or even more preferably subcutaneous injection. Advantageously, such pharmaceutical preparations are available in the form of ready-for-use discardable syringes.

Preferred embodiments of the method of the invention comprise administering to the patient from 25,000 to 100,000 Anti-Xa units daily (titers expressed according to Yin-Wessler method) either by the subcutaneous route (divided into two or three injections per day) or by the intravenous route, in discontinuous administration at regular intervals, or continuously by perfusion, (three times per week). The doses can, in each patient, be standardized or adjusted according to the results of previously effected blood analyses, the nature and the importance of the thrombi, and, generally the patient's state of health. The daily dosages can also be based on USP units. Particularly preferred daily dosages may range from 1250 to 25,000 IU (titers expressed in USP units) by the subcutaneous route, or by the intravenous route. The administrations being done two or three times a day, or by continuous perfusion (three times per week).

The invention will be further illustrated by the following disclosure of pharmacological and clinical data, merely given by way of examples.

I—Study of the thrombolytic activity of LMW heparins with respect to experimental thrombosis in rabbit according to the assay described by WESSLERR et al (J. Appl. Physiol., 1959, 14, 943-946) and modified by FAREED et al (Jap. Pharmacol. Soc. and Science Council of Japan Abstract 785).

1—The assayed products
 (a) standard heparin containing a calcium salt of heparin titrating 170 IU/MG (USP) and 170 IU/mg (Y W) or 170 anti-Xa units (AXa)
 (b) A LMW heparin designated hereinafter as "CY 216" exhibiting an average molecular weight of 6000 extracted from commercial heparin by alcohol fractionation as disclosed in Example 1 of U.S. application Ser. No. 323,567. Titers per mg: less than 50 IU (USP) and 200 anti-Xa units (or AXa).
 (c) A LMW heparin designated hereafter as CY 222 having an average molecular weight of about 4000, obtained by chemical hydrolysis of commercial heparin according to the method disclosed in U.S. application Ser. No. 448,639. Titer per mg: 25 I.U. (USP) and 250 Axa.
 (d) Pentosane polysulfate polyester (SP 54) prepared from beech xylans (Fagus sylvatica)

It should be mentioned that activities measured by USP method and YIN and WESSLER method for heparin and LMW-heparins were expressed and measured in the presence of antithrombin III, the corresponding activities of SP 54 were expressed directly, since they do not depend on antithrombin III (SORIA et al).

Male rabbits of a New Zealand breed weighing from 2.5 to 4 kg were kept under observation for 2 weeks, housed separately in a quiet environment, at a temperature comprised between 16° and 20° C. They were anaesthetized by sub-cutaneous injection at the top of the thigh with 80 mg of Ketamine in 0.8 ml supplemented with 0.4 ml of Xylazine (Rompus Bayer) as muscle relaxant, per kg of body weight. The animals were then placed on their backs. After shaving the front surface of the neck, a longitudinal incision was made and the two jugular veins were bared over about 3 cm/

In each of the two veins a 1.5 cm segment was isolated between two "bull dog" clamps. The downstream clamp was placed first to ensure that the isolated segment should contain a maximum of blood. Eight minutes later, the upstream clamp was removed and so was, again eight minutes later, the downstream one. A thrombus was formed. 30 minutes later, the solution of the product to be tested or an isotonic sodium chloride solution (in the controls) was injected under a reduced volume (0.2 to 2 ml) into the marginal vein of the ear.

A second injection containing 0.4 time the dosage of anaesthetic used for the first injection was administered 75 to 80 minutes after the first anesthesic injection in order to maintain complete anesthesia throughout the experiment.

Finally, 90 minutes after the intravenous injection of the tested products, the vein segments isolated at the start of the test were removed and opened for inspection of their contents.

The sizes of the blood clots present were evaluated according to the scale proposed by Wessler, of 0 to ++++: 0 representing the clot absence and ++++ an exudation-free full clot.

The number of crosses of the two veins of a same animal were added to give an individual score ranging from 0 to 8. The mean value of these individual scores for each group was recorded as the "clot mean" of the group.

The thrombolytic value was calculated as follows, for a group of animals which had received the same products at the same dosage, whereby P was the "clot mean" of a group of animals which had received the isotonic chloride salt solution, and α that of the "clot mean" of the group of animals which have received the product under test.

$$100 \times \frac{P - Q}{P} = \text{thrombolytic value}$$

Under such conditions, the 0 value indicates that no thrombolysis was observed, whereas the 100 value corresponds to complete dissolution of the clots under the experimental abovesaid conditions.

RESULTS

These are indicated in the table below

| PRODUCT INJECTED | Number of Rabbits | DOSAGE per kg. | Average of the clots | Extreme values of the clots | THROMBOLYTIC VALUE |
|---|---|---|---|---|---|
| PHYSIOLOGICAL SALT SOLUTION | 10 | 0.5 ml | 6.15 | 3.5–8 | 0 |
| CALCIPARINE | 10 | 500 UI 500 AXa | 1.95 | 1–4 | 68 |
| CY 216 | 10 | 500 AXa | 0.8 | 0–1.5 | 87 |
| CY 222 | 10 | 500 AXa | 2.75 | 1–5 | 55 |
| PENTOSANE POLYSULFATE | 10 | 2.5 mg 32.5 AXa | 2.65 | 1.5–4 | 57 |

COMMENTS

The tested products neither contributed to the formation of the thrombus (it had been formed 30 minutes before their administration) nor affected its morphology to sensitize it to lysis.

Therefore the observed activities could be attributed especially and perhaps entirely, to fibrinolysis. The LMW heparins tested were highly active particularly at the level of the activators released in the blood circulation.

This conclusion was further supported by the fact that the thrombolytic activity of the most active compound (CY 216) was substantially inhibited in the same test system, when the animals were subjected to a concomitant antifibrinolytic treatment, particularly when they had received an intravenous injection of $\epsilon$-aminocaproic acid (2.5 ml/kg) just before that of CY 216. The value of the clot then obtained in 10 animals was 5.45 (3.5–8) and the corresponding thrombolytic activity of 11 could be deemed as substantially nil.

II—Clinical assay

The following clinical assay is representative of the observations that can be made when a patient affected with thrombosis is subjected to the thrombolytic treatment of the invention.

A 45 years old woman, Mrs B, had been seen for the first time at the hospital in May 1982. She had had in her medical history 5 occurences of thrombo-phlebitis of the lower limbs (the first accident dating bsack to August 1978), a cerebral vascular accident with with hemiparesia and transient blindness of the right eye in 1978. It should be noted that 3 of these phlebitises had occured under anti-vitamin K treatment.

There were family antecedents of thrombotic disease. Mrs B's twin sister was also suffering of phlebitis and pulmonary embolisms. Mrs B's mother died from a pulmonary embolism and two aunts and an uncle from the mother's side also died from a pulmonary embolism. During the year 1982 she suffered under anti-vitamin K treatment another thrombo-phlebitis accident of the left calf. A conventional heparin therapy ws then undertaken for 15 days and followed by an anti-vitamin K treatment associated with platelet anti-aggregating drugs.

During the months of January and February 1982 the persistance of a very sensitive inflammatory cord of the left calf led to envisage repeating the LMW-heparin therapy. The patient was rehospitalized on Mar. 18, 1982 owing to aggravation of the local symptoms.

The biological hemostasis balance carried out in this patient with very considerable personal and family antecedents did not show antithrombin III defficiency. Plasminogen levels and platelets functions were normal. After labelling the platelets with indium their lifespan was found to be normal and they exhibited no site of scintigraphic hyperfixation.

In fact the most significant anomaly was noted at the level of the fibrinolysis after venostasis; a first assay was made on May 21, 1982. Before anoxia, the euglobulin lysis time was of 3 h 50 and the lysis on fibrin plates of 0.2 mm; after 10 min of anoxia the euglobulin lysis time was of 3 h 40 and the lysis on fibrin plates of 0.2 mm. A second test was carried out under the same conditions on May 22nd 1982. Similar results were obtained. A test with DDAVP was hence done on May 25th. No increase in fibrinolytic response after injection of DDAVP was noted. At the end of the year 1982 and at the beginning of 1983, 3 other assays of the fibrinolytic response after venostasis were carried out and each time the fibrinolytic response was nil. A test after 20 min. of anoxia was run again and again proved to be very pathological.

A treatment with CY 222 was started on Mar. 14, 1983 with 1.5 ml 3 times daily. The treatment was then continued yet with a modification of posology.

The whole tolerance was quite good, though with some ecchymoses at the sub-cutaneous injection sites of the CY 222. A feverish intraval between 37°5 and 38 was noted for which no infectious etiology could be ascertained. There was no modification of the hemogram, no hypereosinophily.

But as regards clinical improvements, the painful syndrom of the hardened veinous cord had completely disappeared. Locally there was no sign of inflammation any longer and the cord palpation was less distinct. The local symptomatology was distinctly improved.

The fibrinolytic response by venostasis was perhaps the most outstanding since on March 24, namely 10 days after initiation of the CY 222 treatment, the 10 min. test showed an improvement with euglobulins lysis times of 3 h and lysis of 56 mm$^2$ on fibrin plates before anoxia, and of 2 h 15 and 120 mm$^2$ respectively after anoxia. On March 29th an anoxia test of 20 min. was carried out. A normalization was noted since the euglobulin lysis time and lysis on fibrin plates were of 2 h 50 and 108 mm$^2$ respectively before anoxia and of 50 min and 289 mm$^2$ respectively after anoxia.

The anti-coagulant activity measured by the kaolin cephalin time (KCT) was of about 60 to 65 seconds as compared to a control of 45 seconds.

On March 31, a kinetic study of the anti-Xa activity was carried out after injection of 1.5 ml of CY 222 at 6 AM. At 9 AM the anti-Xa activity was of 2.85 units, at 12 AM of 2.10 units, at 1 PM of 1.75 units, at 3.30 PM of 1.7 units, at 6 PM of 1.3 units and at 9 PM of 1.25 units. Hence very substantial anti-Xa activity had persisted after more than 12 hours after the injection. The KCT remained between 60 and 65 seconds until 9 PM as compared to the 45 seconds for a control.

The patient left the hospital on April 1 with a LMW heparin treatment reduced to a daily dosage of 1 ml of CY 222 twice a day, thus with a total daily dosage of 38000 YW units.

It is of course understood that the claims attached herewith encompass any alternative to the exemplified low molecular weight heparins which have been considered in this application, in relation to their thrombolytic or fibrinolytic activities. Particularly the invention also extends to LMW heparins having thrombolytic, particularly fibrinolytic activity after removal therefrom of their components which can be selectively fixed on antithrombin III fixed on a water-in-soluble support, as disclosed for instance in U.S. application Ser. Nos. 91,164, 323,567 and 448,639 or other references already of record.

We claim:

1. A method for the lysis of blood-thrombus comprising administering LMW heparin in an amount effective to exert thrombolysis in vivo.

2. The method of claim 1 wherein essential constituents of said LMW heparin have molecular weights ranging from about 2000 to 8000.

3. The method of claim 2 wherein said LMW heparin has a Yin-Wessler titer and a USP titer which are respectively in a ratio of at least 3.

4. The method of claim 3 wherein said USP titer is not less than 10 IU/mg.

5. The method of claim 4 wherein said Y W titer and USP titer are in a ratio ranging from 4 to 30.

6. The method of claim 3 wherein said USP titer is not less than 40/mg.

7. The method of claim 6 wherein said YW titer and USP titer are in a ratio ranging from 4 to 30.

8. The method of claim 3 wherein said LMW heparin is administered subcutaneously at dosages ranging from 25,000 to 100,000 AXa per day.

9. The method of claim 1 wherein said LMW heparin is administered intraparenterally.

10. The method of claim 1 wherein said LMW heparin is administered subcutaneously.

11. A method for the lysis of blood-thrombus in vivo which comprises administering LMW heparin in an amount effective to cause lysis of insoluble fibrin in vivo.

12. A method for the lysis of blood-thrombus comprising administering LMW heparin in an amount effective to cause lysis of insoluble fibrin in vivo and causing said lysis of insoluble fibrin.

13. The method of claim 12 wherein the LMW heparin is derived from natural heparin.

14. The method of claim 12 wherein the lysis of insoluble fibrin is caused without creating hemmorhage.

15. The method of claim 12 wherein a therapeutically effective amount of LMW heparin is administered repeatedly.

16. A method for the lysis of a pre-formed blood-thrombus in vivo which comprises administering LMW heparin to a patient having the pre-formed blood-thrombus in an amount effective to cause lysis of the pre-formed blood-thrombus and causing the lysis of the pre-formed blood-thrombus.

* * * * *